United States Patent [19]

Marquis et al.

[11] Patent Number: 4,977,285

[45] Date of Patent: Dec. 11, 1990

[54] RECOVERY OF TERTIARY BUTYL HYDROPEROXIDE AND TERTIARY BUTYL ALCOHOL

[75] Inventors: Edward T. Marquis, Austin; Kenneth P. Keating, Austin; Robert A. Meyer, Austin; John R. Sanderson, Leander, all of Tex.

[73] Assignee: Texaco Chemical Company, White Plains, N.Y.

[21] Appl. No.: 447,934

[22] Filed: Dec. 8, 1989

[51] Int. Cl.$^5$ .................. C07D 301/32; C07D 308/19
[52] U.S. Cl. .................................... 549/529; 549/541; 568/909.8; 568/913
[58] Field of Search ...................... 549/529, 531, 541; 568/909.8, 913

[56] References Cited

U.S. PATENT DOCUMENTS

| | | | |
|---|---|---|---|
| 3,607,669 | 9/1972 | Jubin | 549/541 |
| 3,715,284 | 2/1973 | Burns et al. | 549/541 |
| 3,819,663 | 6/1974 | Levine | 549/529 |
| 3,881,996 | 5/1975 | Schmidt | 549/541 |
| 3,909,366 | 9/1975 | Schmidt et al. | 549/541 |
| 4,140,588 | 2/1979 | Schmidt | 549/541 |
| 4,455,283 | 6/1984 | Sweed | 423/53 |
| 4,705,903 | 11/1987 | Sanderson | 568/922 |
| 4,709,482 | 11/1987 | Sanderson | 568/922 |

FOREIGN PATENT DOCUMENTS 1298253 11/1972 United Kingdom ................. 549/541

Primary Examiner—Richard L. Raymond
Assistant Examiner—Mark W. Russell
Attorney, Agent, or Firm—Jack H. Park; Kenneth R. Priem; Carl G. Ries

[57] ABSTRACT

A heavy distillation fraction comprising tertiary butyl hydroperoxide, tertiary butyl alcohol, impurities and dissolved molybdenum catalyst resulting from the removel of propylene, propylene oxide and tertiary butyl alcohol from an epoxidation reaction product is mixed with about 5 to about 10 wt. %, based on the weight of the heavy liquid distilation fraction, of a lower aliphatic alcohol containing from 1 to 3 carbon atoms to provide a charge mixture, and the charge mixture is:

charged to a falling film evaporator and separator therein, under evaporator operating conditions including a temperature within the range of about 20° to about 150° C. and a pressure of about 1 to about 200 mm Hg., into an overhead vaporized fraction comprising substantially all of the aliphatic alcohol and from about 80 to about 95 wt. % of the heavy distillation fraction charged to the falling film evaporator.

The practice of the present invention will also provide a clear liquid falling film evaporator residue fraction comprising tertiary butyl hydroperoxide, tertiary butyl alcohol, substantially all of the molybdenum contained in the heavy liquid fraction, and impurities.

7 Claims, 1 Drawing Sheet

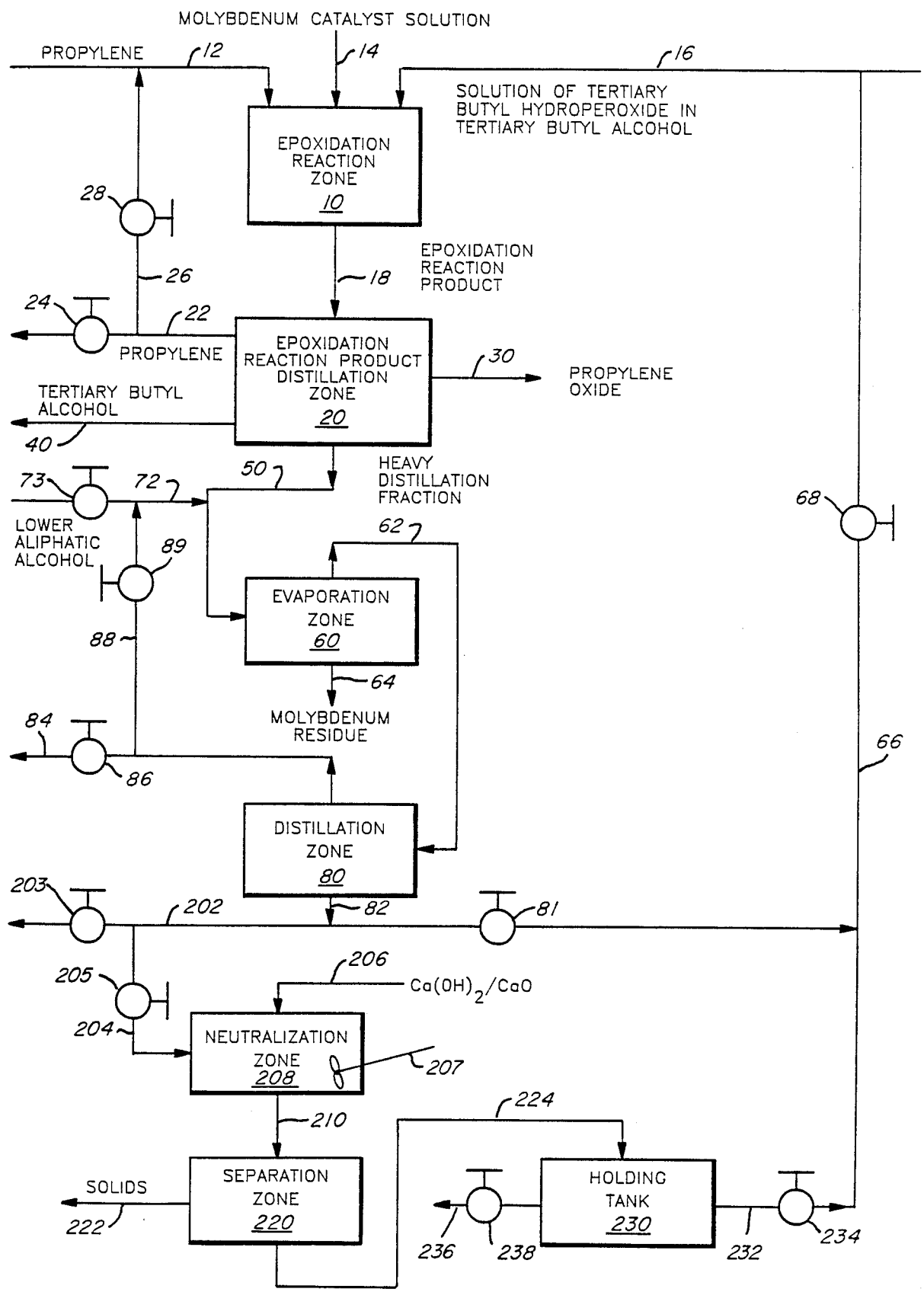

RECOVERY OF TERTIARY BUTYL HYDROPEROXIDE AND TERTIARY BUTYL ALCOHOL

BACKGROUND OF THE INVENTION

1. Field of the Invention

This invention relates to an improvement in the process for resolving the reaction mixture that is formed in preparing propylene oxide and tertiary butyl alcohol by reacting propylene with tertiary butyl hydroperoxide in solution in tertiary butyl alcohol in the presence of a soluble molybdenum catalyst.

The epoxidation reaction mixture that is formed when propylene is reacted with tertiary butyl hydroperoxide in solution in tertiary butyl alcohol in the presence of a soluble molybdenum peroxidation catalyst will normally comprise unreacted propylene, propylene oxide, unreacted tertiary butyl hydroperoxide, the soluble molybdenum catalyst and impurities, including $C_1$ to $C_4$ lower aliphatic carboxylic acids. The reaction mixture is usually separated by distillation into a plurality of fractions including a recycle propylene fraction, a propylene oxide product fraction, a tertiary butyl alcohol product fraction and a heavy liquid distillation fraction containing tertiary butyl alcohol, unreacted tertiary butyl hydroperoxide and impurities, including subtantially all of the dissolved molybdenum catalyst and a portion of the lower aliphatic carboxylic acids impurities.

In accordance with the present invention about 5 to about 10 wt. % of an aliphatic alcohol containing 1 to 3 carbon atoms is added to the heavy liquid distillation fraction.

The resultant mixture is charged to a falling film evaporator and separated therein, under evaporator operating conditions including a temperature within the range of about 20° to about 150° C. and a pressure of about 1 to about 200 mm Hg., into an overhead vaporized fraction comprising substantially all of the aliphatic alcohol and from about 80 to about 95 wt. % of the heavy distillation fraction charged to the falling film evaporator. The overhead fraction will comprise from about 5 to about 10 wt. % of aliphatic alcohol, from about 60 to 90 wt. % of tertiary butyl alcohol, from about 1 to about 20 wt. % of tertiary butyl hydroperoxide and from about 3 to about 15 wt. % of impurities, including at least some of the lower $C_1$–$C_4$ carboxylic acid impurities.

The practice of the present invention will also provide a clear liquid residue fraction comprising tertiary butyl hydroperoxide, tertiary butyl alcohol and impurities, including substantially all of the molybdenum contained in the heavy liquid fraction.

The overhead vaporized fraction is charged to a distillation zone and separated into a lighter aliphatic alcohol distillate fraction and a heavier distillation fraction containing the other components of the overhead vaporized fraction including the tertiary butyl alcohol, the tertiary butyl hydroperoxide and the impurities. The aliphatic alcohol fraction may be recycled to the falling film evaporator as at least a portion of the lower aliphatic alcohol component of the feed mixture, if desired.

PRIOR ART

It is known to react propylene with tertiary butyl hydroperoxide in the presence of a soluble molybdenum catalyst to provide a reaction product comprising propylene oxide and tertiary butyl alcohol. See, for example, Kollar U.S. Pat. No. 3,350,422, Kollar U.S. Pat. No. 3,351,635, and Russell U.S. Pat. No. 3,418,340.

It is also known to prepare soluble molybdenum catalysts to catalyze the reaction as disclosed, for example, in Bonetti et al. U.S. Pat. No. 3,480,563, Shum et al. U.S. Pat. No. 4,607,113, Marquis et al. U.S. Pat. No. 4,626,596, Marquis et al. U.S. Pat. No. 4,650,886, Marquis et al. U.S. Pat. No. 4,703,027, etc.

Kollar U.S. Pat. No. 3,860,662 is directed to an improvement in his basic process relating to the recovery of alcohols from the reaction product, which product is stated to be of an acidic nature, wherein a basic material such as an alkali metal or alkaline earth metal compound is added to the reaction mixture. Kollar U.S. Pat. No. 3,947,500 discloses a method for treating the reaction product formed by the reaction of an organic hydroperoxide with an olefin wherein an organic alcohol is formed as a by-product. It is stated that the alcohol tends to dehydrate and that to at least partially overcome this problem the oxidation reaction product is treated with an alkali metal or an alkaline earth metal compound. Kollar states that the alkali metal or alkaline earth metal compound can be added to the epoxidation reactor or to the reaction product.

Sorgenti U.S. Pat. No. 3,573,226 discloses a method wherein a molybdenum-containing catalyst solution is prepared by incorporating metallic molybdenum into the distillate bottoms fraction of an epoxidation reaction product followed by heating of the resultant mixture in order to form a soluble molybdenum-containing reaction product which can be used to catalyze the epoxidation reaction.

The molybdenum-catalyzed epoxidation of alpha olefins and alpha substituted olefins with hydroperoxides less stable than tertiary butyl hydroperoxide may be accomplished according to U.S. Pat. No. 3,862,961 to Sheng, et al. by employing a critical amount of a stabilizing agent consisting of a $C_3$ to $C_9$ secondary or tertiary monohydric alcohol, such as tertiary butyl alcohol. Citric acid is used to minimize the iron-catalyzed decomposition of the organic hydroperoxide without adversely affecting the reaction between the hydroperoxide and the olefin in a similar oxirane producing process taught by Herzog in U.S. Pat. No. 3,928,393. The inventors in U.S. Pat. No. 4,217,287 discovered that if barium oxide is present in the reaction mixture, the catalytic epoxidation of olefins with organic hydroperoxides can be successfully carried out with good selectivity to the epoxide based on hydroperoxide converted when a relatively low olefin to hydroperoxide mole ratio is used. The alphaolefinically unsaturated compound should be added incrementally to the organic hydroperoxide.

Maurin U.S. Pat. No. 3,931,076 is directed to a method for recovering molybdenum catalyst values from a peroxidation reaction product for recycle. Maurin discloses one of three techniques. In accordance with the first embodiment, the residue fraction is calcined to provide molybdenum trioxide which is then used to prepare a soluble molybdenum compound by reaction with aqueous ammonia. In a second embodiment, the molybdenum-containing fraction is treated with aqueous ammonia without calcining to form an ammonium molybdate which is treated with a polyalcohol to give a molybdic ester. In a third embodiment, the molybdenum-containing fraction is treated with gaseous ammonia in order to form an ammonium molybdate precipitate which can be recovered by filtration.

Harvey U.S. Pat. No. 3,449,217 is directed to a process for the recovery of tertiary butyl hydroperoxide from a mixture comprising tertiary butyl hydroperoxide, tertiary butyl alcohol and organic acids and esters resulting from the liquid phase oxidation of isobutane by a process which minimizes hydroperoxide decomposition. This is done by accomplishing the distillation while the product has an effective pH of below about 9. The patentee teaches the treatment of the reactor effluent with a neutralizing agent such as an alkali metal or an alkaline earth metal hydroxide.

Levine U.S. Pat. No. 3,819,663 is directed to a method for treating a heavy distillation fraction of this nature in order to recover the molybdenum in the concentrated bottoms fraction for recycle to the epoxidation reaction zone as makeup catalyst.

Levine conducts his wiped-film evaporation process under conditions including a temperature of about 550°-650° F. (about 273° to about 330° C.) at atmospheric pressure to obtain his desired residual fraction for recycle as catalyst makeup and a distillate fraction comprising about 85% or more of the heavy distillation fraction. Levine states that the distillate fraction that is thus obtained can be used as a furnace fuel or can be worked up for recovery of the individual components contained therein. However, Levine et al. does not contain any teaching as to how the individual components in the fraction would be obtained.

SUMMARY OF THE INVENTION

In accordance with the present invention, a heavy distillation fraction comprising tertiary butyl hydroperoxide, tertiary butyl alcohol and impurities including dissolved molybdenum catalyst and lower aliphatic carboxylic acids resulting from the removal of propylene, propylene oxide and tertiary butyl alcohol from an epoxidation reaction product is:

mixed with about 5 to about 10 wt. %, based on the weight of the heavy liquid distillation fraction, of a lower aliphatic alcohol containing from 1 to 3 carbon atoms to provide a charge mixture, and the charge mixture is:

charged to a falling film evaporator and fractionated in the falling film evaporator under falling film evaporator operating conditions including a temperature of about 20° to about 150° C. and a pressure of about 1 to about 200 mm Hg in order to obtain an overhead fraction comprising about 80 to about 95 wt. % of the charged heavy distillation fraction which is composed of from about 5 to about 10 wt. % of aliphatic alcohol, from about 60 to 90 wt. % of tertiary butyl alcohol, from about 1 to about 20 wt. % of tertiary butyl hydroperoxide and from about 3 to about 15 wt. % of impurities, including at least some of the carboxylic acid impurities.

The thus-obtained evaporated overhead fraction is charged to a distillation zone where the lower aliphatic alcohol is separated from the other components of the evaporated overhead fraction, and the thus-separated aliphatic alcohol may be recycled as a part of the mixture charged to the falling film evaporator, if desired.

BACKGROUND INFORMATION

It has been surprisingly discovered in accordance with the present invention that when the heavy distillation fraction is subjected to vacuum evaporation in the manner described in admixture with about 5 to about 10 wt. % of a lower aliphatic alcohol containing 1 to 3 carbon atoms under the described evaporation conditions, the normally expected icing of the condenser surfaces will be substantially inhibited.

When propylene is reacted with tertiary butyl hydroperoxide in solution in tertiary butyl alcohol in an epoxidation reaction zone in the presence of a soluble molybdenum catalyst to form propylene oxide and additional tertiary butyl alcohol, an epoxidation reaction mixture is formed which will contain not only unreacted feed components and the desired propylene oxide and tertiary butyl alcohol, but also impurities including the dissolved molybdenum catalyst, oxygen-containing impurities such as ditertiary butyl peroxide, lower aliphatic $C_1$ to $C_4$ carboxylic acids such as formic acid, acetic acid, isobutyric acid, etc., alcohols such as methanol, isopropyl alcohol, tertiary butyl alcohol, etc., esters such as methyl formate, methyl acetate, methyl isobutyrate, etc., ketones such as acetone, etc., aldehydes such as isobutyraldehyde, etc., and hydrocarbon impurities resulting from undesired side reactions of the propylene, such as hydrocarbons containing 6 or more carbon atoms.

Although most of the impurities are originally present in the epoxidation reaction mixture in trace quantities, as the epoxidation reaction mixture is resolved by distillation into a propylene recycle fraction, a propylene oxide product fraction and a tertiary butyl alcohol product fraction, all of which are distillate fractions, the impurites are progressively concentrated in a heavier distillation fraction, such as a distillation fraction having the composition generally set forth in Table I.

TABLE I

| COMPOSITION OF HEAVY DISTILLATION FRACTIONS | |
|---|---|
| Component | Concentration, Wt. % |
| Impurities lighter than TBA | 0.1–2 |
| Tertiary butyl alcohol | 70–90 |
| Impurities heavier than TBA but lighter than TBHP | 1–4 |
| Tertiary butyl hydroperoxide | 2–20 |
| Impurities heavier than TBHP | 3–12 |
| Molybdenum concentration | 500–5,000 ppm |

This fraction is hereafter sometimes referred to, especially in the Working Examples, as the "catalyst bottoms".

In accordance with the present invention, the heavy liquid distillation fraction is mixed with about 5 to about 10 wt. %, based on the weight of the heavy liquid distillation fraction, of a lower aliphatic alcohol containing from 1 to 3 carbon atoms to provide a charge mixture, and the charge mixture is used as a charge stock for a falling film evaporator which is operated under falling film evaporator operating conditions such as a temperature of 20° to 150° C. and a pressure of 1 to about 200 mm Hg. The charge mixture is resolved in the falling film evaporator into an overhead fraction comprising substantially all of the aliphatic alcohol and from about 80 to about 95 wt. % of the heavy liquid residue fraction.

The clear liquid residue fraction that is obtained from the falling film evaporator by the process of the present invention is a liquid fraction that can be handled with comparative ease insofar as its disposal is concerned. Typically, this residual fraction will be sold to a company that reclaims metals from hydrocarbon fractions in order that the molybdenum contained therein may be recovered for reuse.

The evaporated overhead fraction obtained in the falling film evaporator will typically contain substantially all of the aliphatic alcohol contained in the charge mixture and from about 60 to about 90 wt. % of tertiary butyl alcohol, about 1 to about 20 wt. % of tertiary butyl hydroperoxide and, correspondingly, from about 3 to about 15 wt. % of impurities. Among the impurities that will typically be present are impurities such as formic acid, acetic acid and isobutyric acid.

In accordance with the present invention, the evaporated overhead fraction from the falling film evaporator is charged to a distillation zone where the lower aliphatic alcohol is separated from the other components of the evaporated overhead fraction for removal from the system, as desired, or for recycle for admixture with the heavy distillation fraction to form a portion of the charge mixture for the falling film evaporator.

If the evaporated overhead fraction (i.e., a molybdenum-free distillate fraction from which the aliphatic alcohol has been removed) has an acid number of less than about 12, which corresponds to a $C_1$–$C_4$ carboxylic acid content of about 1 wt. % or less, it may be recycled, if desired, to the epoxidation reaction zone. However, if the evaporated overhead fraction is a more heavily contaminated fraction, such as a fraction that contains a greater concentration of $C_1$–$C_4$ carboxylic acids, and is nevertheless recycled to the epoxidation reaction zone, the epoxidation reaction may be adversely affected. The presence of excess quantities of carboxylic acids tends to decrease propylene selectivity to propylene oxide because the increased acidity of the reaction mixture tends to promote side reactions of the propylene oxide with alcohols such as tertiary butyl alcohol that are present in the epoxidation reaction mixture. Also, the selectivity of TBHP to PO is reduced.

In this situation, the more heavily contaminated molybdenum-free distillate fraction may be treated so as to remove an amount of acidic impurities sufficient to permit recycle to the epoxidation reaction zone.

Thus, the more heavily contaminated lighter evaporated condensate fraction can be treated with calcium oxide and/or hydroxide in the manner disclosed and claimed in copending Marquis et al. U.S. Pat. application Ser. No. 07/400,901, filed Aug. 30, 1989 and entitled "Removal of Acidic Contaminants from Tertiary Butyl Hydroperoxide" (D#80,817). When this is to be done, the more heavily contaminated lighter evaporated condensate fraction can be charged to a neutralization zone and treated with about ½ to 1 equivalents of calcium oxide and/or calcium hydroxide, based on the carboxylic acid content of the condensate fraction to form a slurry of partially precipitated carboxylic acid impurities. The precipitate may be separated from the treated product by any suitable means such as centrifugation, filtration, etc., to provide a filtrate that is suitable for reycle to the epoxidation reaction zone.

BRIEF DESCRIPTION OF THE DRAWING

In the drawing, the figure is a schematic drawing of a preferred reaction and purification sequence that may be used in the practice of the present invention.

DESCRIPTION OF THE PREFERRED EMBODIMENT

Turning now to the drawing, there is shown a schematic flowsheet illustrating a preferred method of practicing the process of the present invention.

An epoxidation reaction zone 10 is provided and propylene is charged thereto by a line 12 together with a soluble molybdenum catalyst charged by a line 14 and a solution of tertiary butyl hydroperoxide and tertiary butyl alcohol charged by a line 16.

The epoxidation reaction is an epoxidation reaction of the type disclosed by Kollar U.S. Pat. No. 3,351,653 as further elaborated upon, for example, in British patent specification No. 1,298,253 wherein propylene is reacted with tertiary butyl hydroperoxide under reaction conditions including a reaction temperature within the range of about 180° to about 300° F., a pressure of about 300 to about 1000 psig. and, more preferably, a temperature of about 220° F. to about 280° F. and a pressure of about 500 to about 800 psig.

The soluble molybdenum catalyst charged to the epoxidation reaction zone by the line 14 may be an epoxidation catalyst of the type known in the art such as those disclosed by the Kollar patent or the British patent or by Marquis et al. U.S. Pat. No. 4,626,596, U.S. Pat. No. 4,650,886, U.S. Pat. No. 4,654,427, or U.S. Pat. No. 4,758,681. The Marquis et al. patents are directed to molybdenum/alkanol complexes such as solutions of molybdenum compounds in ethylene glycol which contain a high concentration of molybdenum and are particularly useful as catalysts in the epoxidation reaction. Marquis et al. teach, for example, the epoxidation of propylene with tertiary butyl hydroperoxide with their catalyst under epoxidation conditions including a temperature of 50° to 180° C. and a use of propylene to tertiary butyl hydroperoxide ratios within the range of about 0.9:1 to about 3.0:1.

Suitably, the tertiary butyl hydroperoxide that is charged to the epoxidation reaction zone 10 by way of line 16 is about a 40 to about 75 wt. % solution of tertiary butyl hydroperoxide in tertiary butyl alcohol. The catalyst is charged to the epoxidation reaction zone 10 by the charge line 14 in an amount such as to provide from about 50 to about 1000 ppm of molybdenum, based on the total of the reactants charged and, more preferably, from about 200 to 600 ppm. The reaction is preferably conducted at superatmospheric pressure such as a pressure of about 300 to 1000 psig.

When the reaction is conducted on a continuous basis, as illustrated in the drawing, the feed materials are charged to the epoxidation reaction zone 10 through the lines 12, 14 and 16 at rates sufficient to maintain the desired concentration of reactants and an equivalent volume of epoxidation reaction mixture is withdrawn from the epoxidation reaction zone 10 by way of a discharge line 18. The reaction product discharged by the line 18 will normally comprise unreacted propylene, a minor amount of unreacted tertiary butyl hydroperoxide, propylene oxide, tertiary butyl alcohol, including tertiary butyl alcohol formed by the reaction of the tertiary butyl hydroperoxide with propylene, the molybdenum catalyst and impurities such as propane, propionaldehyde, acetone, methanol, isopropanol, water, acetaldehyde, methyl formate, acetic acid, formic acid, isobutyric acid, hydrocarbons containing 6 or more carbon atoms and high boiling residue components.

The reaction product 18 is charged to an epoxidation reaction product distillation zone 20 where it is separated by distillation into desired fractions in accordance with methods known to those skilled in the art. For example, the distillation sequence disclosed in British Patent No. 1,298,253 may be used.

One of the distillate products that is recovered in the zone 20 is a propylene fraction which is discharged by a line 22 controlled by a valve 24 and provided with a branch line 26 controlled by a valve 28 in order to permit the recycle of unreacted propylene to the epoxidation reaction zone 10 through the propylene charge line 12.

Another distillate fraction that is obtained is a propylene oxide product fraction 30 which is discharged by the line 30.

The propylene oxide fraction may be purified in a propylene oxide purification zone (not shown) by known techniques such as, for example, those disclosed in Burnes et al. U.S. Pat. No. 3,715,284, Schmidt et al. U.S. Pat. No. 3,909,366, Schmidt U.S. Pat. No. 3,881,996, Jubin U.S. Pat. No. 3,607,669, Schmidt U.S. Pat. No. 3,843,488 or Schmidt U.S. Pat. No. 4,140,588.

Another product that is recovered from the epoxidation reaction product distillation zone 20 is a tertiary butyl alcohol distillate product 40 which may be further purified, if desired, to remove oxygenated impurities therefrom by catalytic treatment as disclosed, for example, in Sanderson et al. U.S. Pat. No. 4,704,482, Sanderson et al. U.S. Pat. No. 4,705,903 or Sanderson et al. U.S. Pat. No. 4,742,149.

A heavy distillation fraction 50, usually a bottoms fraction, is also discharged from the epoxidation reaction product distillation zone 20. As described by Levine U.S. Pat. No. 3,819,663 and Sweed U.S. Pat. No. 4,455,283, the heavy distillation fraction will contain substantially all of the molybdenum catalyst initially charged to the epoxidation reaction zone 10 by way of the line 14. The heavy distillation fraction 50 will contain other products such as tertiary butyl hydroperoxide, tertiary butyl alcohol and impurities including oxygenates lighter than tertiary butyl alcohol such as acetaldehyde, acetone, isopropyl alcohol, etc., oxygenates heavier than tertiary butyl alcohol but lighter than tertiary butyl hydroperoxide, and residue components heavier than tertiary butyl hydroperoxide such as propylene glycol tertiary butyl ethers, hydrocarbons containing 6 or more carbon atoms, etc. As indicated, the heavy distillation fraction 50 will also contain carboxylic acids such as formic acid, acetic acid and isobutyric acid.

In accordance with the present invention, about 5 to about 10 wt. %, based on the weight of the heavy liquid distillation fraction, of a lower aliphatic alcohol containing 1 to 3 carbon atoms, such as methanol, ethanol, propanol, or isopropanol, and preferably propanol, is charged by way of a charge line 72 controlled by a valve 73 to the line 50 leading to a falling film evaporator 60.

Also in accordance with the present invention, the falling film evaporator 60, which is preferably a wiped film evaporator, is operated under conditions including a temperature within the range of about 20° to about 150° C. and a pressure within the range of about 1 to about 200 mm Hg; an average residence time of the charge mixture in the falling film evaporator 60 being such that from about 80 to about 95 wt. % of the material charged by way of the line 50 is taken overhead as a distillate fraction by way of the line 62; the remaining 5-20 wt. % of the material charged by way of the line 50 being discharged from the falling film evaporator 60 by way of a bottoms discharge line 64. The fraction 64 will contain substantially all of the molybdenum initially discharged from the epoxidation reaction zone 10.

It has been surprisingly discovered in accordance with the present invention that when the charge mixture 50 is subjected to falling film evaporation in the manner described and under the conditions described that the small amount of lower alcohol added (5 to 10%) prevents icing of TBA on the condenser walls.

The vaporized fraction discharged from the wiped film evaporator by the line 62 will contain substantially all of the propanol charged to the wiped film evaporator 60 through the line 50 and will also comprise about 60 to about 90 wt. % of tertiary butyl alcohol, about 1 to about 20 wt. % of tertiary butyl hydroperoxide and from about 3 to about 15 wt. % of impurities.

In accordance with the present invention, the vaporized fraction 62 from the falling film evaporator 60 is charged to a distillation zone 80 where it is separated into a molybdenum-free distillate fraction discharged by a line 84 controlled by a valve 86 for discharge from the system or for recycle through a branch line 88 controlled by a valve 89 leading to the propanol charge line 72. The heavy distillation fraction (e.g., bottoms fraction 82) is substantially free from propanol and comprises the tertiary butyl alcohol, tertiary butyl hydroperoxide and other impurities charged to distillation column 80 by line 62.

If the molybdenum-free distillate fraction discharged from the distillation zone 80 by the line 82 has an acid number of about 12 or less (i.e., contains about 1 wt. % or less of lower $C_1$–$C_4$ aliphatic carboxylic acids) it may be routed to the tertiary butyl hyroperoxide charge line 16 by a tertiary butyl hydroperoxide recycle line 66 controlled by a valve 68. As indicated above, if the acid number of the molybdenum-free distillate fraction 82 is more than about 12 and it is recycled to epoxidation reaction zone 10, the selectivity of the propylene to propylene oxide and TBHP to propylene oxide may be adversely effected. In this situation, the molybdenum-free distillate fraction 82 may be discarded from the system by a branch line 202 controlled by a valve 203. However, in accordance with a preferred embodiment of the present invention, the molybdenum-free distillate fraction 82 is routed by a branch line 204 controlled by a valve 205 to a neutralization zone 208 in order to reduce the acid number to an acceptable level of about 12 or less.

In accordance with this embodiment, the molybdenum-free distillate fraction 82 is treated in the manner described and claimed in copending Marquis et al. U.S. Pat. application Ser. No. 07/400,901, filed Aug. 30, 1989 and entitled "Removal of Acidic Contaminants from Tertiary Butyl Hydroperoxide" (D# 80,817).

Thus, an autoclave 208 equipped with suitable agitation means such as an impeller 207 may be provided. The fraction 204 is continuously charged to the autoclave 208 together with about ½ to about 1 equivalents of powdered calcium oxide and/or calcium hydroxide, based on the carboxylic acids contained in the fraction 204, the calcium oxide and/or calcium hydroxide being continuously charged to the autoclave 208 by way of a charge line 206. Appropriate neutralization conditions are established in the autoclave 208 such as a temperature of about 70° to about 100° C., a residence time of about ¼ to about 5 hours, and an appropriate pressure, such as atmospheric pressure. As a consequence, the calcium oxide and/or calcium hydroxide will partially react with the carboxylic acids present in the autoclave 208 to form a precipitate. The resultant slurry is discharged from the autoclave 208 by an autoclave discharge line 210 leading to a separation zone 220 (e.g., a centrifugation zone, a filtration zone, etc.) where the slurry is separated into a solids fraction comprising calcium salts of precipitated carboxylic acids which is discharged by a line 222 and a filtrate fraction comprising a partially purified stream of tertiary butyl alcohol and tertiary butyl hydroperoxide having an acid number of about 12 or less which is discharged by a discharge line 224 leading to a holding tank 230. If desired, the partially purified filtrate 224 comprising tertiary butyl alcohol and tertiary butyl hydroperoxide in the holding tank 230 may be discharged therefrom by a line 232 controlled by a valve 234 for recycle to the epoxidation reaction zone 10 by way of tertiary butyl hydroperoxide recycle line 66. If desired, the filtrate 224 may be discharged from the holding tank 230 by a line 236 controlled by a valve 238 for another purpose such as, for example, for use as a boiler fuel.

The invention will be further illustrated by the following specific examples which are given by way of example and not as limitation on the scope of this invention.

EXAMPLES

The table is a multi-part table.

Experiment 6195-83 is a controlled evaporation conducted in a standard rotary evaporator with the feed and conditions as described in the table. Note in this control run there was extensive freezing and crystallization of the largely TBA overhead. Pure TBA freezes at about 25° C. This can present serious problems on a commercial scale. In experiments 6195-89, 6195-88, 6195-91, and 6195-92, n-propanol was added to the feed (epoxidation catalyst bottoms) and at the 5% level or greater (4.26%) there was no freezing in the condenser coils or neck of the receiver flask. This addition of n-propanol did not appear to adversely affect other material balances, such as the TBHP balance, the molybdenum balance, or acid balance as measured by acid number.

In summary, the addition of n-propanol to the epoxidation catalyst bottoms before final evaporation and catalyst concentration will prevent freezing in the condensers (heat exchangers) which could seriously upset a commercial operation.

TABLE II

CONCENTRATION OF EPOXIDATION CATALYST BOTTOMS USING A ROTARY OR WIPED-FILM EVAPORATOR ADDITION OF N-PROPANOL TO THE FEED TO PREVENT FREEZING IN THE OVERHEAD CONDENSER OR RECEIVER

| | Starting Material #, Amt Used, Properties | | | | | Balance Data - Fed | | | | | |
|---|---|---|---|---|---|---|---|---|---|---|---|
| NB Run # | ETM NB # | Grams Fed/ Charged | Wt. % TBHP | ppm Moly | Acid # mg KOH | Grams TBHP Fed | Grams Moly Fed | Moles Acid Fed | Grams Formate Fed | Grams Acetate Fed | Grams Isobutyrate Fed |
| 6195-83 12/23/86 | 5815-74-1 | 500.0 | 6.61 | 721 | 13.20 | 33.050 | 0.3605 | .117647 | 3.4000 | 1.4000 | 0.2500 |
| 6195-89 1/9/87 | 5815-74-1 n-propanol | 500.0 10.0 | 6.61 | 721 | 13.20 | 33.050 | 0.3605 | .117647 | 3.4000 | 1.4000 | 0.2500 |
| 6195-88 1/8/87 | 5815-74-1 n-propanol | 500.0 25.0 | 6.61 | 721 | 13.20 | 33.050 | 0.3605 | .117647 | 3.4000 | 1.4000 | 0.2500 |
| 6195-91 1/14/87 | 5815-74-1 n-propanol | 500.0 25.0 | 6.61 | 721 | 13.20 | 33.050 | 0.3605 | .117647 | 3.4000 | 1.4000 | 0.2500 |
| 6195-92 1/15/87 | 5815-74-1 n-propanol | 500.0 50.0 | 6.61 | 721 | 13.20 | 33.050 | 0.3605 | .117647 | 3.4000 | 1.4000 | 0.2500 |

TABLE III

CONCENTRATION OF EPOXIDATION CATALYST BOTTOMS USING A ROTARY OR WIPED-FILM EVAPORATOR ADDITION OF N-PROPANOL TO THE FEED TO PREVENT FREEZING IN THE OVERHEAD CONDENSER OR RECEIVER

| | Evaporator Data | | | Overall Material Balance | | | | | | | | |
|---|---|---|---|---|---|---|---|---|---|---|---|---|
| NB Run # | Bath Temp °C. (Type of Evapor.) | Time Hrs | Vac. mm Hg | Cold Trap Grams | Cold Trap (% of Total Rec'd) | Overhead Grams | Overhead- (% of Total Rec'd) | Over head- F.P. C | Btms Grams | Btms % of Total Rec'd | Btms % Moly | Total Grams Rec'd | Grams Rec'd (% of Grams Fed) |
| 6195-83 | 24-60 60 Rotary/Wet Ice Consenser Extensive Freezing/Cryst. in Condenser & Rec Flask | 0.62 1.50 | 50 50 | 2.3 | 0.5 | 449.1 | 90.2 | 13.75 | 46.4 | 9.3 | 0.75 | 497.8 | 99.6 |
| 6195-89 | 24-60 60 Rotary/Wet Ice Condenser No Freezing in Cond Coils Some Freezing in Neck RF | 0.88 1.50 | 50 50 | 1.3 | 0.2 | 456.7 | 89.9 | 11.50 | 50.1 | 9.9 | 0.74 | 508.1 | 99.6 |
| 6195-88 | 24-60 60 Rotary/Wet Ice Condenser No Freezing in Cond Coils No Freezing in Neck of RF | 0.92 1.50 | 50 50 | 0.5 | 0.1 | 472.9 | 90.3 | 8.89 | 50.5 | 9.6 | 0.67 | 523.9 | 99.8 |

TABLE III-continued
CONCENTRATION OF EPOXIDATION CATALYST BOTTOMS USING A ROTARY OR WIPED-FILM EVAPORATOR ADDITION OF N-PROPANOL TO THE FEED TO PREVENT FREEZING IN THE OVERHEAD CONDENSER OR RECEIVER

| | Evaporator Data | | | Overall Material Balance | | | | | | | | |
|---|---|---|---|---|---|---|---|---|---|---|---|---|
| NB Run # | Bath Temp °C. (Type of Evapor.) | Time Hrs | Vac. mm Hg | Cold Trap Grams | Cold Trap (% of Total Rec'd) | Over-head Grams | Over head- (% of Total Rec'd) | Over head- F.P. C | Btms Grams | Btms % of Total Rec'd | Btms % Moly | Total Grams Rec'd | Grams Rec'd (% of Grams Fed) |
| 6195-91 | 24–60 60 Rotary/Wet Ice Condenser No Freezing in Cond Coils No Freezing in Neck of RF | 0.47 1.50 | 50 50 | 0.6 | 0.1 | 473.1 | 90.4 | 7.99 | 49.8 | 9.5 | 0.70 | 523.5 | 99.7 |
| 6195-92 | 24–60 60 Rotary/Wet Ice Condenser No Freezing in Cond Coils No Freezing in Neck of RF | 0.83 1.50 | 50 50 | 0.9 | 0.2 | 498.8 | 90.9 | −16.26 | 48.8 | 8.9 | 0.84 | 548.5 | 99.7 |

TABLE IV
CONCENTRATION OF EPOXIDATION CATALYST BOTTOMS USING A ROTARY OR WIPED-FILM EVAPORATOR ADDITION OF N-PROPANOL TO THE FEED TO PREVENT FREEZING IN THE OVERHEAD CONDENSER OR RECEIVER

| | TBHP Balance | | | | | | MO Balance | |
|---|---|---|---|---|---|---|---|---|
| NB Run # | Grams TBHP Overhead | TBHP Overhead (% of Total Rec'd) | Grams TBHP in Btms | TBHP in Btms (% of Total Rec'd) | Total Grams TBHP Rec'd | Total (% of TBHP Fed) | Grams Moly in Btms | Moly in Btms (% of Moly Fed) |
| 6195-83 | 18.772 | 60.9 | 12.036 | 39.1 | 30.808 | 93.2 | 0.3480 | 96.5 |
| 6195-89 | 16.030 | 54.8 | 13.246 | 45.2 | 29.277 | 88.6 | 0.3707 | 102.8 |
| 6195-88 | 15.653 | 54.7 | 12.953 | 45.3 | 28.606 | 86.6 | 0.3384 | 93.9 |
| 6195-91 | 16.606 | 56.4 | 12.834 | 43.6 | 29.440 | 89.1 | 0.3486 | 96.9 |
| 6195-92 | 15.413 | 55.0 | 12.615 | 45.0 | 28.028 | 84.8 | 0.4099 | 113.7 |

TABLE V
CONCENTRATION OF EPOXIDATION CATALYST BOTTOMS USING A ROTARY OR WIPED-FILM EVAPORATOR ADDITION OF N-PROPANOL TO THE FEED TO PREVENT FREEZING IN THE OVERHEAD CONDENSER OR RECEIVER

| | Acid Balance | | | | | | | |
|---|---|---|---|---|---|---|---|---|
| NB Run # | Moles Acid Cold Trap | Acid Cold Trap (% of Total Rec'd) | Moles Acid Overhead | Acid Overhead (% of Total Rec'd) | Moles Acid in Btms | Acid in Btms (% of Total Rec'd) | Total Moles Acid Rec'd | Moles Acid Rec'd (% of Acid Fed) |
| 6195-83 | .000067 | 0.1 | .073329 | 59.8 | .049129 | 40.1 | .122525 | 104.1 |
| 6195-89 | .000078 | 0.1 | .069523 | 56.2 | .054029 | 43.7 | .123630 | 105.1 |
| 6195-88 | N.E.S.* | N.E.S.* | .053106 | 50.0 | .053111 | 50.0 | .106217 | 90.3 |
| 6195-91 | N.E.S.* | N.E.S.* | .057430 | 51.9 | .053191 | 48.1 | .110621 | 94.0 |
| 6195-92 | N.E.S.* | N.E.S.* | .048724 | 47.2 | .054445 | 52.7 | .103218 | 87.7 |

*N.E.S. = Not enough sample

TABLE VI
CONCENTRATION OF EPOXIDATION CATALYST BOTTOMS USING A ROTARY OR WIPED-FILM EVAPORATOR ADDITION OF N-PROPANOL TO THE FEED TO PREVENT FREEZING IN THE OVERHEAD CONDENSER OR RECEIVER

| | Formate Balance | | | | | | |
|---|---|---|---|---|---|---|---|
| NB Run # | Grams Formate Cold Trap | Formate Cold Trap (% of Total Rec'd) | Grams Formate Overhead | Formate Overhead (% of Total Rec'd) | Grams Formate in Btms | Formate in Btms (% of Total Rec'd) | Total Grams Formate Rec'd | Formate Rec'd (% of Formate Fed) |
| 6195-83 | 0.0009 | 0.03 | 1.5718 | 53.0 | 1.3920 | 47.0 | 2.9647 | 87.2 |
| 6195-89 | N.E.S.* | N.E.S.* | 1.3701 | 46.1 | 1.6032 | 53.9 | 2.9733 | 87.4 |
| 6195-88 | N.E.S.* | N.E.S.* | 1.2768 | 48.4 | 1.3635 | 51.6 | 2.6403 | 77.7 |
| 6195-91 | N.E.S.* | N.E.S.* | 1.2774 | 47.8 | 1.3944 | 52.2 | 2.6718 | 78.6 |
| 6195-92 | 0.0005 | 0.02 | 1.3966 | 53.3 | 1.2225 | 46.7 | 2.6196 | 77.0 |

*N.E.S. = Not enough sample

TABLE VII

CONCENTRATION OF EPOXIDATION CATALYST BOTTOMS USING A ROTARY OR WIPED-FILM EVAPORATOR ADDITION OF N-PROPANOL TO THE FEED TO PREVENT FREEZING IN THE OVERHEAD CONDENSER OR RECEIVER

Acetate Balance

| NB Run # | Grams Acetate Cold Trap | Acetate Cold Trap (% of Total Rec'd) | Grams Acetate Overhead | Acetate Overhead (% of Total Rec'd) | Grams Acetate in Btms | Acetate in Btms (% of Total Rec'd) | Total Grams Acetate Rec'd | Acetate Rec'd (% of Acetate Fed) |
|---|---|---|---|---|---|---|---|---|
| 6195-83 | 0.0005 | 0.03 | 0.7186 | 44.9 | 0.8816 | 55.1 | 1.6007 | 114.3 |
| 6195-89 | N.E.S.* | N.E.S.* | 0.6850 | 41.8 | 0.9519 | 58.2 | 1.6369 | 116.9 |
| 6195-88 | N.E.S.* | N.E.S.* | 0.6621 | 37.3 | 1.1110 | 62.7 | 1.7731 | 126.6 |
| 6195-91 | N.E.S.* | N.E.S.* | 0.6150 | 39.4 | 0.9462 | 60.6 | 1.5612 | 111.5 |
| 6195-92 | 0.0003 | 0.02 | 0.7981 | 46.2 | 0.9291 | 53.8 | 1.7275 | 123.4 |

*N.E.S. = Not enough sample

TABLE VIII

CONCENTRATION OF EPOXIDATION CATALYST BOTTOMS USING A ROTARY OR WIPED-FILM EVAPORATOR ADDITION OF N-PROPANOL TO THE FEED TO PREVENT FREEZING IN THE OVERHEAD CONDENSER OR RECEIVER

Isobutyrate Balance

| NB Run # | Grams Isobutyrate Cold Trap | Isobutyrate Cold Trap (% of Total Rec'd) | Grams Isobuty-rate Overhead | Isobutyrate Overhead (% of Total Rec'd) | Grams Isobuty-rate in Btms | Isobutyrate in Btms (% of Total Rec'd) | Total Grams Isobuty-rate Rec'd | Isobuty Rec'd (% of Isobuty Fed) |
|---|---|---|---|---|---|---|---|---|
| 6195-83 | 0.0009 | 0.1 | 0.1796 | 28.9 | 0.4408 | 70.9 | 0.6213 | 248.5 |
| 6195-89 | N.E.S.* | N.E.S.* | 0.1827 | 28.4 | 0.4609 | 71.6 | 0.6436 | 257.4 |
| 6195-88 | N.E.S.* | N.E.S.* | 0.1892 | 25.4 | 0.5555 | 74.6 | 0.7447 | 297.9 |
| 6195-91 | N.E.S.* | N.E.S.* | 0.1892 | 38.8 | 0.2988 | 61.2 | 0.4880 | 195.2 |
| 6195-92 | 0.0004 | 0.1 | 0.1995 | 37.1 | 0.3374 | 62.8 | 0.5373 | 214.9 |

*N.E.S. = Not enough sample

Having thus described our invention, what is claimed is:

1. In a process for the preparation of propylene oxide and tertiary butyl alcohol wherein propylene and tertiary butyl hydroperoxide are reacted in an epoxidation reaction zone in solution in tertiary butyl alcohol in the presence of a soluble molybdenum catalyst to provide an epoxidation reaction product comprising unreacted propylene, unreacted tertiary butyl hydroperoxide, tertiary butyl alcohol, dissolved molybdenum catalyst and impurities, including lower aliphatic $C_1$-$C_4$ carboxylic acids, and wherein the epoxidation reaction product is resolved into product fractions in a distillation zone including a distillate propylene fraction, a distillate propylene oxide fraction, a distillate tertiary butyl alcohol fraction and a heavy liquid distillation fraction composed primarily of tertiary butyl hydroperoxide, tertiary butyl alcohol, the dissolved molybdenum catalyst, and impurities including lower aliphatic $C_1$-$C_4$ carboxylic acids, the improvement which comprises:

adding to said heavy liquid distillation fraction from about 5 to about 10 wt. %, based on the weight of said heavy liquid distillation fraction, of a lower aliphatic alcohol containing about 1 to about 3 carbon atoms to provide a mixture, charging said mixture to a falling film evaporator and resolving said mixture therein under evaporator operating conditions including a temperature of about 20° to about 150° C. and a pressure of about 1 to about 200 mm Hg. into an evaporated overhead fraction comprising about 80 to about 95 wt. % of the charged heavy liquid distillation fraction and a liquid residue fraction, said evaporated overhead fraction containing substantially all of the said lower aliphatic alcohol initially charged to said falling film evaporator and also containing from about 60 wt. % to about 90 wt. % of tertiary butyl alcohol, about 1 wt. % to about 20 wt. % of tertiary butyl hydroperoxide and, correspondingly, about 3 wt. % to about 15 wt. % of impurities, including a portion of said lower aliphatic $C_1$-$C_4$ carboxylic acid impurities, said liquid residue fraction comprising tertiary butyl hydroperoxide, tertiary butyl alcohol and impurities, including substantially all of the molybdenum contained in said heavy liquid fraction, and separating said lower aliphatic alcohol from the other components of said evaporated overhead fraction and recycling said separated lower aliphatic alcohol to said falling film evaporator as at least a portion of the lower aliphatic alcohol comprising said mixture.

2. A process as in claim 1 wherein the falling film evaporator is a wiped film evaporator.

3. A process as in claim 1 wherein said lower aliphatic alcohol is propanol.

4. In a process for the preparation of propylene oxide and tertiary butyl alcohol wherein propylene and tertiary butyl hydroperoxide are catalytically reacted in an epoxidation reaction zone in solution in tertiary butyl alcohol in the presence of a soluble molybdenum catalyst to provide an epoxidation reaction product comprising unreacted propylene, unreacted tertiary butyl hydroperoxide, tertiary butyl alcohol, dissolved molybdenum catalyst and impurities including lower aliphatic $C_1$-$C_4$ carboxylic acid impurities, methyl esters thereof, alcohols, ketones and hydrocarbons, and wherein the epoxidation reaction product is resolved into product fractions in a distillation zone including a distillate propylene recycle fraction, a distillate propylene oxide product fraction, a distillate tertiary butyl alcohol product fraction and a heavy liquid distillation fraction composed primarily of tertiary butyl hydroperoxide, tertiary butyl alcohol, the dissolved molybdenum catalyst, and impurities including lower aliphatic $C_1$-$C_4$ carboxylic acids, the improvement which comprises:

adding to said heavy liquid distillation fraction from about 5 to about 10 wt. %, based on the weight of said heavy liquid distillation fraction, of a lower aliphatic alcohol containing about 1 to about 3 carbon atoms to provide a mixture, charging said mixture to a wiped film evaporator and resolving said mixture therein under evaporation conditions including a temperature of about 20° to about 150° C. and a pressure of about 1 to about 200 mm Hg., into an evaporated overhead fraction and a clear liquid residue fraction, said evaporated overhead fraction containing substantially all of said lower aliphatic alcohol and also containing about 80 to about 95 wt. % of the charged heavy distillation fraction and comprising unreacted tertiary butyl hydroperoxide, tertiary butyl alcohol, and impurities including methyl esters thereof, alcohols, ketones and hydrocarbons, said clear liquid residue fraction comprising tertiary butyl hydroperoxide, tertiary butyl alcohol, substantially all of the molybdenum contained in said heavy liquid fraction, and impurities, and separating said lower aliphatic alcohol from the other components of said evaporated overhead fraction and recycling said separated lower aliphatic alcohol to said wiped film evaporator as at least a portion of the lower aliphatic alcohol comprising said mixture.

5. A process as in claim 4 wherein said lower aliphatic alcohol is propanol.

6. A process as in claim 4 wherein said evaporated overhead fraction has an acid number of not more than about 12 and is recycled to said epoxidation reacton zone.

7. A process as in claim 4 wherein said evaporated overhead fraction has an acid number of more than about 12, is charged to a neutralization zone and treated therein with about ½ to 1 equivalent of calcium oxide and/or calcium hydroxide per equivalent of said lower aliphatic $C_1$-$C_4$ carboxylic acid impurities contained therein to provide a slurry of precipitated solids including calcium salts of said $C_1$-$C_4$ carboxylic acid impurities, wherein said slurry is charged to a separation zone and separated therein to provide a solids fraction comprising calcium salts of said lower aliphatic carboxylic acids and a substantially solids-free filtrate having an acid number of less than about 12 and comprising tertiary butyl hydroperoxide, tertiary butyl alcohol and a reduced quantity of said carboxylic acid impurities, and wherein said filtrate is recycled to said epoxidation reaction zone.

* * * * *